United States Patent [19]

Sie

[11] Patent Number: 5,219,891
[45] Date of Patent: * Jun. 15, 1993

[54] PROCESS FOR THE PRODUCTION OF METHANOL

[75] Inventor: Swan T. Sie, Amsterdam, Netherlands

[73] Assignee: Shell Oil Company, Houston, Tex.

[*] Notice: The portion of the term of this patent subsequent to Jun. 1, 2010 has been disclaimed.

[21] Appl. No.: 783,443

[22] Filed: Oct. 28, 1991

[30] Foreign Application Priority Data

Oct. 29, 1990 [GB] United Kingdom ............ 9023464

[51] Int. Cl.$^5$ .................... C07C 27/06; C07C 27/08
[52] U.S. Cl. ............................. 518/706; 518/712
[58] Field of Search ................................ 518/706

[56] References Cited

U.S. PATENT DOCUMENTS 3,598,527 8/1971 Quartulli et al. ............... 518/706
4,235,799 11/1980 Wentworth et al. ............ 518/706

OTHER PUBLICATIONS

Westerterp et al., Ind. Eng. Chem. Res., 1989, 28, 763-771.
Post et al., Chemeca 1988, Australia's Bicentennial International Conference for the Process Industries, Sidney, Aug. 28-31, 1988.
Saito et al, AIChE Symposium Series No. 262 vol. 84, pp. 102-113, 1988.

Primary Examiner—Howard T. Mars
Attorney, Agent, or Firm—Y. Grace Tsang

[57] ABSTRACT

A process for the production of methanol by reacting a gaseous mixture comprising hydrogen and carbon monoxide in the presence of a catalyst composition in the form of a fluidized bed whilst cooling, characterized in that the catalyst composition is present in a plurality of interconnected fluidized bed sections whereby each section is cooled by at least one heat exchanger and whereby the temperature in the highest section is reduced to below the highest temperature in a lower section.

6 Claims, 1 Drawing Sheet

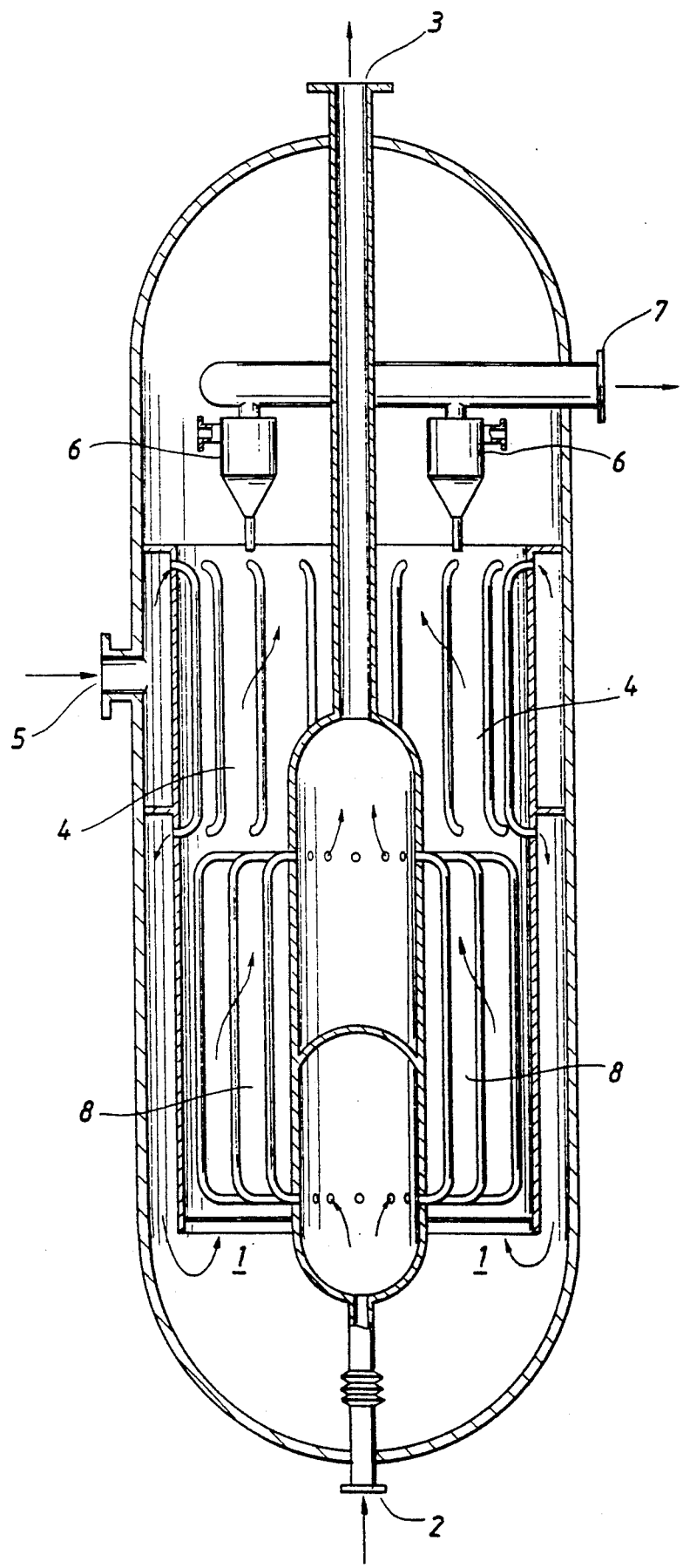

PROCESS FOR THE PRODUCTION OF METHANOL

FIELD OF THE INVENTION

The invention relates to a process for the production of methanol by reacting a gaseous mixture comprising hydrogen and carbon monoxide in the presence of a catalyst composition in a fluidized bed while cooling.

BACKGROUND OF THE INVENTION

Processes for the production of methanol by reacting a gaseous mixture comprising hydrogen and carbon monoxide in the presence of a catalyst composition in a fluidized bed have been disclosed in the prior art.

A lecture reporting work by Y. Saito, M. Kuwa and O. Hashimoto during the 1987 Annual Meeting of the American Institute of Chemical Engineers, New York, Nov. 15-20, 1978, entitled "Development of a fluidized-bed methanol synthesis process" discloses a process using a reactor with the catalyst in a fluidized bed, cooled by means of a cooling jacket covering the surrounding wall of the bed. The temperature was adjusted by the temperature of the coolant (water being converted into high pressure steam). The temperature in the fluidized bed was essentially constant. This process requires high space velocities and causes a considerable drop in pressure over the reactor, the conversion per pass was about 16%. Unconverted carbon monoxide and hydrogen were recompressed and recycled through the reactor inlet.

A lecture reporting work by M.F.M. Post; S. T. Sie and J. M. Oelderik during the Chemeca'88 (Australia's Bicentennial International Conference for the Process Industries), Sydney Aug. 28-31, 1988, entitled "Synthesis of methanol in a fluidized bed of catalyst" discloses fluidized bed methanol synthesis at bench scale with conversions up to 60% at 8.1 MPa and 250° C. (523° K.) and good catalyst stability. For commercial scale operations the reported conversions were too low, however. The temperature in the fluidized bed in these experiments was essentially constant.

Also there is Chemical Week, 36 (Apr. 16, 1980) disclosing a process known as Chem Systems' three-phase process in which an inert liquid was used to fluidize the heterogeneous catalyst and to remove the heat of reaction. Good conversions per pass are claimed. However, the inert liquid caused mass transport problems and affected the reaction rate adversely. Moreover the process requires separation of methanol from the entrained liquid. The temperature in the reaction mixture was essentially constant, especially because the liquid has good temperature equalizing properties.

Cheap methanol in very large quantities is a valuable product as a fuel and a starting material for further chemical processing. Therefore there is a need for an economically attractive industrial bulk manufacturing process, using cheap starting materials and operating under attractive economical, environmental and safe conditions, i.e. using rather simple equipment and resulting in a significant reduction of the methanol cost price. Therefore considerable research and development efforts have been made for a further improved methanol manufacturing process.

The formation of methanol from hydrogen and carbon monoxide is a strongly exothermic equilibrium reaction so that relatively high operating pressures and temperatures are required for reasonable reaction rates, but under such reaction conditions the attainable conversion is strongly limited by the thermodynamic equilibrium. Finding a satisfactory compromise as to the reaction conditions between reaction rate and conversion percentage is therefore difficult. Effective control of the reaction temperature across the catalyst bed provide to be especially important.

An object of the present invention is the development of an industrial process for methanol manufacture with satisfactory conversion percentages in relatively simple equipment.

SUMMARY OF THE INVENTION

The present invention provides a process for the production of methanol by reacting a gaseous mixture comprising hydrogen and carbon monoxide with a fluidized catalyst composition present in a plurality of interconnected fluidized bed sections whereby each section is cooled by at least one heat exchanger and whereby the temperature in the highest section is reduced to below the (highest) temperature in a lower section.

BRIEF DESCRIPTION OF THE DRAWING

The sole drawing shows a reactor suitable for the practice of this invention.

DETAILED DESCRIPTION OF THE PREFERRED EMBODIMENTS

In a preferred embodiment of the invention the highest section of the catalyst bed is kept at a temperature which is 10-100 centigrades lower than that of the highest temperature in a lower section of the catalyst bed. More preferably the lower sections are cooled by a heat exchanger converting water into high pressure steam and the highest section cooled by a heat exchanger cooled with a gaseous mixture of hydrogen and carbon monoxide, in particular the feedgas to the reactor. It is further recommended that the feedgas/reaction mixture flows through the heat exchanger in countercurrent with each other.

The reaction temperature depends on the activity of the catalyst composition employed. In the case of an active catalyst the temperature may be as low as 100° C., but may be as high as 350° C. Usually the (average) reaction temperature in the lower section of the fluidized catalyst bed is between 200° C. and 300° C., preferably between 220° C. and 280° C.

Although it is preferred to include the various sections of the fluidized catalyst bed in one reactor this is not required according to this invention and in fact each fluidized catalyst bed section can be present in a separate reactor of a series of interconnected reactors. The terms "highest" and "lower" refer to the one reactor embodiment but have a corresponding meaning with respect to incoming feed gas and effluent when more than one reactor is employed. Any fluidized bed sections in between the lowest and highest section should preferably be cooled to a temperature above the temperature of the highest section.

The gaseous mixture fed into the reactor comprises hydrogen and carbon monoxide in a molar ratio $H_2:CO = 1$ to $3:1$, preferably between 1.5 to 2.5:1, more preferably around 2:1. Synthesis gas obtained by partial oxidation of methane with oxygen ($H_2:CO = 2:1$), is a recommended starting material, synthesis gas obtained by reforming of methane and/or carbon dioxide ($H_2CO = 3:1$) can also be used.

According to a preferred embodiment of the invention the incoming gas feed acts as a coolant passing through a heat exchanger in a higher part of the catalyst bed.

The pressure in the reaction zones is usually in the range of from 5 to 35 MPa and again this is dependent on the activity of the catalyst composition employed and with active catalysts pressures below 10 MPa can be used.

The catalyst composition employed in the practice of this invention may suitably comprise, inter alia copper/zinc optionally promoted with another element such as aluminum or chromium, precious metals like palladium and/or platinum on a carrier such as e.g. carbon, silica and/or alumina. Catalyst materials comprising copper and zinc, optionally promoted with another element are preferred. Particle size and distribution of the catalyst material must be suitable for fluidized bed technique or made so e.g. by grinding and sieving. A particle size below 0.4 millimeter is generally suitable. Also resistance of the catalyst composition towards attrition is important.

The temperature of the lowest section or lower sections of the catalyst bed is conveniently adjusted by means of the pressure and temperature of the water fed in the heat exchanger(s) and by temperature and pressure of the high pressure steam produced.

In a preferred embodiment of the present invention a plurality of fluidized catalyst bed reactors producing methanol are in series with interstage removal of methanol from the reaction mixture.

Removal of methanol can be e.g. be effected by cooling and condensation or by adsorption/absorption to a solvent. Cooling and condensation are preferred and are conveniently effected in a heat exchanger connected to a gas/liquid separator. The gaseous phase from which methanol has been removed can then be directly recycled or alternatively fed into a next reactor in case a series of reactors are employed (without reheating or recompressing).

On a practical scale it is recommended to use a series of reactors with interstage removal of methanol in which each next reactor has a smaller capacity than the previous one. Alternatively it is feasible to use e.g. groups of parallel reactors in series wherein the number of parallel reactors in each next group (and consequently their total capacity) is smaller than in the previous group and where interstage removal of methanol is effected between the groups of reactors.

One of the advantages achieved by the present invention is that the temperature of the highest section of the fluidized bed and the effluent of the reactor can be lower than the mean temperature of the reactor which results in a higher temperature and consequently higher reaction rate in the lower section(s) of the fluidized bed and a more favorable position of the thermodynamic equilibrium and consequently a higher conversion percentage in the upper section and effluent.

A further advantage of the process according to the invention is that it is possible to replenish the catalyst while the reaction is operated, catalyst stability requirements are therefore relieved and it is possible to carry out the reaction at a relatively high temperature in the lower section(s) of the catalyst bed providing additional room to improve space-time-yield. In addition this provides the possibility to increase the temperature (quality) of the high pressure steam generated.

The invention also provides a reactor suitable for carrying out the process of the invention which reactor comprises a facility for fluidizing a catalyst material so as to form a fluidized bed, which consists of a plurality of sections, each provided with at least one separate heat exchanger provided with inlets and outlets for different coolants and optionally a gas feed pre-heater.

A particular favorable reactor for the practice of this invention is represented by the attached drawing. This features a facility (perforated carrier plate) 1 for a catalyst bed in two temperature sections of which the lower section has a heat exchanger 8 with inlet 2 suitable for boiler feed water and an outlet 3 suitable for high pressure steam and the highest section has a heat exchanger 4 suitable for heating incoming synthesis gas (syngas) through inlet 5; at the top of the reactor there are one or more cyclones 6 suitable for removing catalyst fines and an outlet for product gas 7.

When the process according to the present invention is operated it is possible by selecting suitable reaction conditions and an active catalyst, such as $H_2CO = 67:32$, T = 250°–200° C., P = 8 MPa and a reduced Cu-ZnO-$Cr_2O_3$-catalyst (atomic ratio of the metals 25:48:27) having a particle size of 0.1 millimeter, to obtain a degree of conversion of more than 60% per pass through a reactor as described above, this can be followed by interstage removal of methanol formed, preferably by cooling and condensation and the remaining gaseous phase can then be passed through a another similar reactor, which reactor can be smaller than the first one, the procedure of interstage removal of methanol formed and using the gaseous phase as the feed gas for another reactor can be repeated a number of times. After multiple stages an overall yield of at least 90% of the feed gas of the first reactor can thus be obtained and methanol formed separated by interstage removal between the reactors. A methanol purity of over 98% can be obtained.

It is clear that in case the incoming feed gas of the first reactor is e.g. synthesis gas containing more than 2 moles of hydrogen per mole of carbon monoxide that after three or more stages and interstage removal of methanol a hydrogen rich effluent gas is obtained. By applying membrane separation to this hydrogen rich gas it is possible to obtain chemically pure hydrogen.

The ranges and limitations provided in the instant specification and claims are those which are believed to particularly point out and distinctly claim the instant invention. It is, however, understood that other ranges and limitations that perform substantially the same function is substantially the same manner to obtain the same or substantially the same result are intended to be within the scope of the instant invention as defined by the instant specification and claims.

What is claimed is:

1. In a process for production of methanol by reacting a gaseous mixture comprising hydrogen and carbon monoxide at a temperature from 100° C. to about 350° C. in the presence of a catalyst composition, comprising copper and zinc, contained in a fluidized bed, wherein said gaseous mixture provided as a feed stream has a molar ratio of $H_2:CO = 1$ to 3:1, the improvement which comprises:

(a) contacting said gaseous mixture with said fluidized bed comprising a plurality of interconnected sections arranged in sequence in the direction of flow of the gaseous mixture, and (b) cooling each section of said fluidizing bed by at least one heat exchanger whereby the temperature of the last section in sequence of the fluidized bed is lower than the highest temperature of the preceding section(s).

2. The process according to claim 1, wherein the last section in sequence of said fluidized catalyst bed is kept at a temperature which is 10–100 centrigrades lower than the highest temperature in the preceding section(s).

3. The process according to claim 1, wherein the cooling of at least one of the sections of the catalyst bed other than the last section in sequence is provided by a heat exchanger which converts water into high pressure steam, and the the cooling of the last section in sequence is provided by a heat exchanger cooled with the feed stream gaseous mixture of hydrogen and carbon monoxide.

4. The process according to claim 1, wherein a plurality of fluidized bed reactors in series are employed and methanol formed is removed in between the reactors.

5. In a process for production of methanol by reacting a gaseous mixture comprising hydrogen and carbon monoxide at a temperature from 100° C. to 350° C. in the presence of a catalyst composition, comprising copper and zinc, contained in a fluidized bed, wherein said gaseous mixture provided as a feed stream has a molar ratio of $H_2:CO = 1$ to 3:1, the improvement which comprises:

(a) contacting said gaseous mixture with said fluidized bed comprising a plurality of interconnected sections arranged in sequence in the direction of flow of the gaseous mixture, (b) cooling such section of said fluidized bed by at least one heat exchanger, wherein the first section in sequence of the catalyst bed is cooled by a heat exchanger which converts water into high pressure steam, and the last section in sequence is cooled by a heat exchanger cooled with the feed stream gaseous mixture of hydrogen and carbon monoxide whereby the temperature of the last section in sequence of the fluidized bed is kept at a temperature which is 10–100 centrigrades lower than the highest temperature in the preceding section(s) and whereby the feed stream gaseous mixture is warmed to a higher temperature, (c) passing said warmed feed stream gaseous mixture, exiting from the heat exchanger of the last section in sequence of the catalyst bed from (b), to the first section of the catalyst bed, and (d) employing a plurality of fluidized bed reactors in series operating in the same manner as steps (a), (b) and (c), and removing the methanol formed in between the reactors.

6. In a process for production of methanol by reacting a gaseous mixture comprising hydrogen and carbon monoxide in a fluidized bed reactor at a temperature from 100° C. to 350° C. in the presence of a catalyst composition, comprising copper and zinc, contained in the fluidized bed reactor, wherein said gaseous mixture provided as a feed stream to the reactor has a molar ratio of $H_2:CO = 1$ to 3:1, the improvement which comprises:

(a) contacting said gas mixture with said fluidized bed reactor comprising a plurality of interconnected sections arranged vertically in sequence in the reactor in the direction of flow of the gaseous mixture, (b) cooling each section of said fluidized bed by at least one heat exchanger, wherein the lowest section of the catalyst bed is cooled by a heat exchanger which converts water into high pressure steam, and the highest section of the catalyst bed is cooled by a heat exchanger cooled with the feed stream gaseous mixture of hydrogen and carbon monoxide whereby the temperature of the highest section of the fluidized bed is kept at a temperature which is 10–100 centrigrades lower than the highest temperature in the lower section(s) and whereby the feed stream gaseous mixture is warmed to a higher temperature, (c) passing said warmed feed stream gaseous mixture, exiting from the heat exchanger of the highest section of the catalyst bed from (b), to the lowest section of the catalyst bed, and (d) employing a plurality of said fluidized bed reactors in series operating in the same manner as in steps (a), (b), and (c), and removing the methanol formed in between the reactors.

* * * * *